(12) United States Patent
McGuire

(10) Patent No.: US 6,398,793 B1
(45) Date of Patent: Jun. 4, 2002

(54) DISPOSABLE DERMAL CURETTE

(75) Inventor: Joseph McGuire, Stanford, CA (US)

(73) Assignee: Acuderm Inc., Ft. Lauderdale, FL (US)

( * ) Notice: Subject to any disclaimer, the term of this patent is extended or adjusted under 35 U.S.C. 154(b) by 0 days.

(21) Appl. No.: 09/637,402

(22) Filed: Aug. 11, 2000

(51) Int. Cl.⁷ .............................................. A61B 17/32
(52) U.S. Cl. ...................................... 606/131; 606/160
(58) Field of Search ................................ 606/131, 160, 606/84, 159, 161, 162; 30/164.9; 132/75.4

(56) References Cited

U.S. PATENT DOCUMENTS

| | | | | |
|---|---|---|---|---|
| 466,097 A | * | 12/1891 | Guess | 132/75.4 |
| 872,567 A | * | 12/1907 | Langstaff | 65/319 |
| 2,574,654 A | * | 11/1951 | Moore | 606/161 |
| 3,502,082 A | * | 3/1970 | Chatfield | 606/160 |
| 4,044,770 A | * | 8/1977 | Ocel et al. | 606/161 |
| 4,221,222 A | * | 9/1980 | Detsch | 606/160 |
| 5,116,346 A | | 5/1992 | Yeh | |
| 5,250,061 A | * | 10/1993 | Michelson | 606/160 |

* cited by examiner

Primary Examiner—Eduardo C. Robert
(74) Attorney, Agent, or Firm—Rockey, Milnamow & Katz, Ltd.

(57) ABSTRACT

A disposable dermal curette for scraping lesions from the surface of a patient's skin, comprising a generally cylindrical plastic handle having a proximal end portion, a distal end portion and a mid-section portion therebetween. The curette has a substantially flattened annular working element attached to the handle, the working element having a hoe-shape, substantially planer configuration and arcuate walls projecting therefrom to the handle and attached thereto. The arcuate walls extend from the planar cutting surface having a radius sufficient to minimize gouging as the cutting surface is moved along the skin to remove lesions therefrom.

4 Claims, 1 Drawing Sheet

DISPOSABLE DERMAL CURETTE

BACKGROUND OF THE INVENTION

This invention relates generally to medical devices for scraping skin lesions, and more particularly to an improved disposable dermal curette which is particularly effective in the removal of flat lesions or lesions of large area.

A dermal curette is a device used by medical practitioners for scraping growths, such as skin cancers, warts, actinic keratoses and seborrheic keratoses, from the surface of the skin. Generally, such devices are simple in construction, with a handle and a working element having a sharpened edge which is used to scrape the surface of the skin and remove the lesion. The working element is commonly an annular or ring-like configuration providing a curved or circular sharpened edge as the working surface of the curette.

There are generally three basic types of dermal curettes: the Fox Curette, the Piffard Curette and the eye curette. The Fox Curette is a device having a flat handle, usually metallic, with a generally cylindrical arm extending from the handle, also metallic, terminating in a working element having an oval or annular cutting edge. The Piffard Curette has a large metal handle tapering toward the cutting edge inwardly from the end of the handle, with a generally cylindrical metallic arm extending from the handle and terminating in a working element having an oval or rounded-loop cutting edge. The Piffard Curette is further provided with grooves or ribbed surfaces extending longitudinally along the length of the handle of the curette. The eye curette is similar in design to the Fox Curette, but has a working element which is a dish with a sharp edge rather than loop-shaped, resulting in a working edge to provide a scooping action. The eye curette also has grooves or ribbed surfaces which extend circumferentially around the width of the handle.

Variations of the dermal curettes described above are available and are identified and marketed as the Buck, Skeele or Heath curettes. These curettes, as well as the ones described above, are reusable, that is, designed and manufactured for repeated use after sterilization and, when necessary, resharpening.

Dermal curettes of such design have been, and are currently being, used by physicians in medical procedures for the removal of lesions and unhealthy growths from the surface of the skin of a patient. Generally, in such procedures, the physician anesthetizes the area, removes the lesion with a scraping action utilizing a dermal curette, and then cauterizes or electro-desiccates the area scraped. Sometimes the procedure is reversed in part and, after anesthetizing the area, the lesion is desiccated and then scraped using a curette. Ideally, only the lesions or unhealthy growths are removed in the scraping procedure with minimal destruction of the remaining healthy tissues.

As with many medical procedures, the effectiveness of such scraping procedures depends upon two interrelated factors, namely, the skill of the physician and the design of the tool used. Abnormalities of the skin, such as cancers, warts, actinic keratoses and seborrheic keratoses, differ to the touch from healthy tissues. Therefore, the experienced physician relies on the sense of touch during the scraping procedure and "feels" the difference between healthy and unhealthy tissues. With the proper tools, the physician can use his sense of touch to judge the depth of scraping necessary to remove only the unhealthy tissues, leaving the healthy tissues relatively unharmed.

In view of the sensory-dependent nature of such procedures, the design of the tool used is of critical importance. The curette must have working element which is sharp enough to cut rather than pull and distort the tissue. Reusable curettes, like those described above, dull easily and hold a sharp edge variably. Thus, a curette which has a working element of consistent sharpness, which the disposable curette of the present invention provides because of its one-time use, is needed. Furthermore, the curette should have a handle of sufficient weight to provide the balance necessary to allow the physician to properly "feel" the lesion, and an overall design which provides the physician with maximum control of the tool in use.

In U.S. Pat. No. 5,116,346, which issued in May of 1992, there is described an improved dermal curette which overcomes many of the foregoing disadvantages. The curettes described and claimed in that patent provide proper balance and design to allow a physician to exert the maximum control in scraping lesions from the surface of the patient's skin. The curettes disclosed there, like most dermal curettes in use today, have an oval or round annular configuration, either in a loop or cup shape. As a result, such curettes are not optimal in the removal of lesions of greater area. Thus there is a need for curettes having a planar cutting edge which may be used effectively in the removal of such large flat lesions. It has been proposed in U.S. Pat. Nos. 4,651,735, 3,934,591, 4,665,915, 4,270,540 and 4,221,222 to employ dermal curettes having a relatively flat cutting surface. Unfortunately, however, most of such curettes and like cutting tools are either not disposable, and hence subject to the disadvantages outlined above, or have removable blades in which the blade is disposable. Nonetheless, such cutting tools do not provide the necessary cutting control and the ability to effectively remove flat lesions with a fewer number of passes and less gouging or formation of grooves in the treated tissue.

SUMMARY OF THE INVENTION

It is an object of this invention to provide an improved dermal curette having a substantially flat or planar cutting surface which can be utilized in scraping lesions and growths from the surface of a patient's skin.

It is another object of this invention to provide an improved dermal curette having a substantially flat or planar working edge of consistent sharpness which is capable of producing a scraping action when used in removing lesions from the surface of a patient's skin.

It is a further object of this invention to provide an improved dermal curette having a substantially flat cutting surface having the proper balance and design to allow the user maximum control in scraping lesions from the surface of a patient's skin so that the experienced physician need scrape only to the depth necessary, with minimal gouging or groove formation, while minimizing potentially disfiguring results.

The present invention relates to a disposable dermal curette designed to be used in scraping lesions and unhealthy tissue from the surface of a patent's skin. The curette includes a generally cylindrical plastic handle having a proximal end portion and a distal end portion, with the proximal end portion tapering inwardly to a point near a flat-nosed end of the handle. The working element which engages the skin is a substantially flattened annular working element attached to the flat-noted end of the handle. Unlike disposable dermal curettes previously employed, the curette of the present invention utilizes a working element having a flattened, substantially planar configuration. The flattened annular thus forms a cutting surface along the base of the working element to scrape lesions and unhealthy tissue from a patient's skin.

In the most preferred embodiment of the invention, the handle includes a mid-section portion between the proximal and distal end portions. For control and balance, the distal end portion of the handle is provided with a textured surface, preferably grooved or ribbed surfaces, extending longitudinally the distal end portion. The mid-section portion of the handle is preferably defined by a recessed flat surface extending length-wise along the top of the mid-section portion. The remainder of the mid-section portion is generally cylindrical in shape. For maximum control and proper balance, the proximal end portion may further be provided with a textured surface like the distal end portion. The mid-section portion, in one embodiment, may be further provided with a finely textured surface around its width.

DETAILED DESCRIPTION OF THE INVENTION

Figure 1:
FIG. 1 shows a side view of the dermal curette of the present invention.
Figure 2:
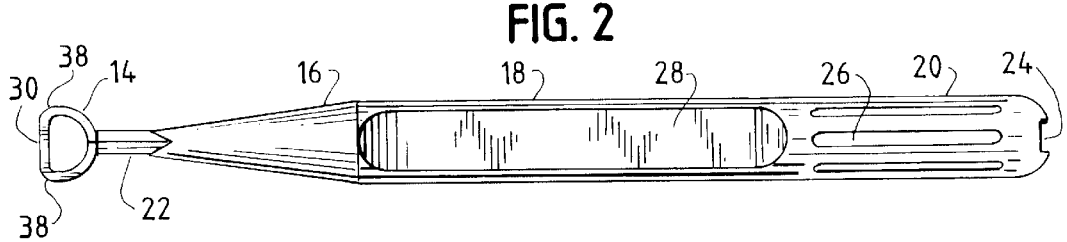
FIG. 2 shows a top view of the dermal curette of the present invention.
Figure 3:
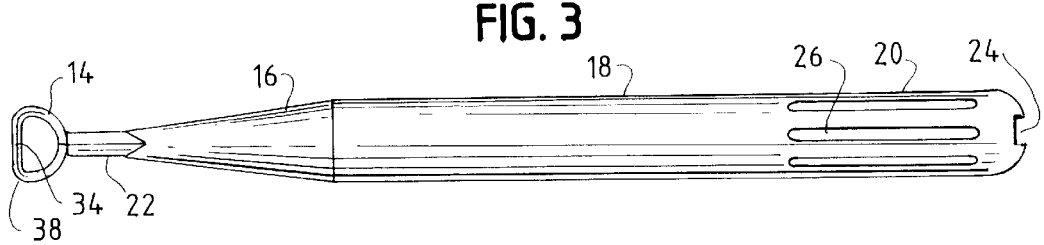
FIG. 3 shows a bottom view of the dermal curette of the present invention.
Figure 4:
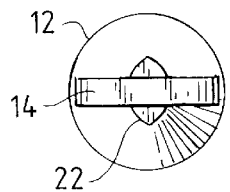
FIG. 4 shows a front end view of the dermal curette of the present invention.

Referring first to FIGS. 1 through 3, the dermal curette 10 of the present invention may be seen as a whole as including a handle 12 and a working element 14. The handle 12 is generally cylindrical in shape and includes a proximal end portion 16, a mid-section portion 18 and a distal portion 20. The proximal end portion 16 tapered inwardly from a point near the mid-section portion to a point near the proximal end of the handle, and terminates in a generally flat-nosed end 22. In a preferred embodiment, the proximal end portion may also be provided with a textured surface, preferably grooved or ribbed surfaces such as grooved or ribbed surfaces extending length-wise from a point near the mid-section portion 18 to a point near the flat-nosed end of the handle 22.

As is also shown in FIGS. 1 through 3, the distal end portion 20 of handle 12 is generally cylindrical in shape and preferably terminates in a notched end 24, as shown in FIGS. 2 and 3. The distal end portion is provided with a textured surface, preferably grooved or ribbed surfaces 26 which extend length-wise from a point near the mid-section portion 18 to a portion near its notched end 24. The grooved or ribbed surfaces 26 may be, but need not be, extended to the distal end portion, or may extend to the edges of the notched end 24.

Located between the proximal end portion 16 and the distal end portion 20 is the mid-section portion 18. As shown in greater detail in FIG. 2, the mid-section portion 18 is provided with a flat end surface 28 on the top of the handle, with the flat end surface 28 being recessed relative to the adjacent sections of the proximal end portion 16 and the distal end portion 20. Thus, the flat end surface 28 of the mid-section portion 18 lies below the adjacent sections of the proximal and distal end portions and is opposite to the side of the cutting edge.

As further shown in FIGS. 1 and 3, the remainder of the mid-section portion 18 is generally cylindrical in shape. In one embodiment, the mid-section portion 18 may be further provided with a textured surface, preferably finely grooved or ribbed surfaces extending around the width of its cylindrical surface. The textured surface may also extend through the crests of the grooved or ribbed surfaces 24 of the distal end portion 20.

Figure 5:
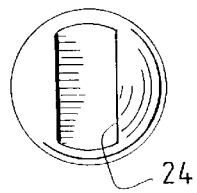
FIG. 5 shows a rear end view of the dermal curette of the present invention.
Figure 6:
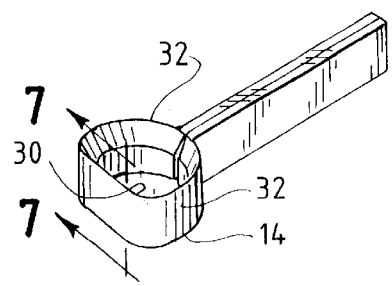
FIG. 6 shows a detailed view of the working surface of the dermal curette of the present invention.
Figure 7:
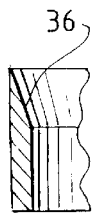
FIG. 7 is a sectional view of the metal working element of the dermal curette of the present invention taken along the lines 7—7 in FIG. 6.

As shown generally in FIGS. 2, 3 and 6, the working element 14 extends to the flat-nosed end portion 22 of the handle and is attached thereto. The working element 14, as is perhaps best shown in FIG. 6, is a substantially flattened annular having a planar cutting surface 30 integral with lateral cylindrical side walls 32. The cutting edge 34 is along the bottom wall 30 and includes a beveled surface 36 as shown in FIG. 7. As is well-understood by those skilled in the art, the cutting edge 34, shown in cross section in FIG. 5, is provided by sharpening methods generally known to those skilled in the art and sharpened to a degree sufficient to allow the curette to be used in scraping lesions and unhealthy tissue from the surface of the patient's skin.

It is an important concept of the present invention that the side or lateral surfaces 32 and the bottom surface 34 be joined each to the other by arcuate edge portions 38. Those arcuate edge portions preferably have a radius sufficient to minimize gouging as the cutting surface 34 moves along the skin to remove lesions and unhealthy tissue therefrom.

As will be appreciated by those skilled in the art, the handle 12 of the dermal curette of the present invention is preferably made from plastic materials by injection molding techniques well-known by those skilled in the art. High impact polystyrene is frequently the preferred plastic material. The handle is designed, and should be molded with the features described above, to provide a properly balanced curette which allows for maximum control in the hand of the physician. The textured surfaces of the proximal end portion, and optional textured surfaces of the mid-section and distal end portions, as well as the recessed surface of the mid-section, provide traction and gripping surfaces. They accordingly reduce the potential for slippage when the curette is used. Also, the material and design of the handle provide the physician-user with a curette having the weight necessary to properly balance the curette, feel the lesion and determine the depth of scraping necessary to remove unhealthy tissues while leaving healthy tissues intact.

As will also be appreciated by those skilled in the art, the working element 14 is metal in composition, preferably any of a variety of stainless steel surgical steels. The cutting edge is preferably single beveled, ground and honed. The degree of sharpness may be controlled by a primary grind of a 7 degree angle and the double-honed angle of 32 degrees.

It will be understood by those skilled in the art that, while the invention has been described with reference to a preferred embodiment, various changes may be made in the details of structure and materials of construction without departing from the spirit of the invention.

What is claimed is:

1. A disposable curette for use in treating lesions on the skin comprising:

a generally elongate plastic handle having a proximal end portion and a distal end portion, the proximal end portion of the handle tapering inwardly to a point near a flatnosed end of the handle;

a substantially flattened annular working element attached to the flat-nosed end of the end portion of the handle and having lateral arcuate walls, said working element having a substantially planar cutting surface integral with the lateral arcuate walls attached to the flat-nosed end of the handle attached thereto, said arcuate walls having a radius sufficient to minimize gouging as the cutting surface is moved along the skin to remove lesions therefrom.

2. The dermal curette of claim 1 wherein the handle is composed of high impact polystyrene.

3. The dermal curette of claim 1, wherein the plastic handle also includes top side and a mid-section portion between said end portions, the mid-section portion having a flat end surface on the top side of the handle, with the flat end surface being recessed relative to the adjacent sections of the proximal end and distal end portions, the end portions being generally cylindrical in shape.

4. The dermal curette of claim 1 wherein the distal end portion of the handle is generally cylindrical in shape and has a textured surface extending substantially along its entire length.

* * * * *